(12) United States Patent
Giuliani et al.

(10) Patent No.: US 10,675,239 B2
(45) Date of Patent: Jun. 9, 2020

(54) VEGETABLE EXTRACT TO PREVENT AND TREAT HAIR LOSS

(71) Applicant: GIULIANI S.P.A., Milan (IT)

(72) Inventors: Giammaria Giuliani, Montagnola (CH); Anna Benedusi, Milan (IT); Barbara Marzani, Carbonara al Ticino (IT)

(73) Assignee: GIULIANI S.P.A., Milan (IT)

( * ) Notice: Subject to any disclaimer, the term of this patent is extended or adjusted under 35 U.S.C. 154(b) by 0 days.

(21) Appl. No.: 16/477,694

(22) PCT Filed: Jan. 11, 2018

(86) PCT No.: PCT/EP2018/050656
§ 371 (c)(1),
(2) Date: Jul. 12, 2019

(87) PCT Pub. No.: WO2018/130613
PCT Pub. Date: Jul. 19, 2018

(65) Prior Publication Data
US 2019/0358148 A1 Nov. 28, 2019

(30) Foreign Application Priority Data

Jan. 12, 2017 (IT) .......................... 102017000003045

(51) Int. Cl.
*A61K 8/9789* (2017.01)
*A61Q 7/00* (2006.01)

(52) U.S. Cl.
CPC .............. *A61K 8/9789* (2017.08); *A61Q 7/00* (2013.01)

(58) Field of Classification Search
None
See application file for complete search history.

(56) References Cited

U.S. PATENT DOCUMENTS 9,498,429 B2 * 11/2016 Giuliani ................... A61K 8/97
2015/0056255 A1 * 2/2015 Ragot ....................... A23F 5/36
424/401

FOREIGN PATENT DOCUMENTS

WO WO2015/063678 A 5/2015

OTHER PUBLICATIONS

Pinto et al., "209 Galeopsis Segetum Necker Extracts for the Prevention and Treatment of Hair", The Journal of Investigative Dermatology: Official Journal of the Society for Investigative Dermatology and the European Society for Dermatological Research, 136(a): S196 (Sep. 1, 2016).
Subirade I., Fernandez Y., Periquet A., Mitjavila S., "Catechin Protection of 3T3 Swiss Fibroblasts in Culture Under Oxidative Stress," Biol. Trace Elem. Res., 47(1-3), 313-319 (1995).
Kutuk O., Adli M., Poli G., Basaga H., "Resveratrol protects against 4-HNE induced oxidative stress and apoptosis in Swiss 3T3 fibroblasts," Biofactors, 20(1):1-10 (2004).
Mosmann T., "Rapid Colorimetric Assay for Cellular Growth and Survival: Application to Proliferation and Cytotoxicity Assays." J. Immunol. Methods, 65(1-2), 55-63 (1983).
Rajapakse N., Mendis E., Byun HG, Kim SK, "Purification and in vitro antioxidative effects of giant squid muscle peptides on free radical-mediated oxidative systems," J. NutrBiochem., 16(9):562-569 (2005).
Coda R., Rizzello CG, Pinto D., Gobbet M., "Selected Lactic Acid Bacteria Synthesize Antioxidant Peptides during Sourdough Fermentation of Cereal Flours," Appl. Environ. Microbial., 78(4):1087-1096 (2012).
Tobi SE, Paul N., McMillan TJ, "Glutathione modulates the level of free radicals produced in UVA-irradiated cells," J. Photoch. & Photobio. B. Biol., 57(2-3):102-112 (2000).
Chomczynski P., Mackey K., "Modification of the TRI reagent procedure for isolation of RNA from polysaccharide- and proteoglycan-rich sources," Biotechniques, 19(6):942-5 (1995).

* cited by examiner

*Primary Examiner* — Terry A McKelvey
*Assistant Examiner* — Catheryne Chen
(74) *Attorney, Agent, or Firm* — Abelman, Frayne & Schwab

(57) ABSTRACT

The present invention relates to the use of a plant extract from the genus *Galeopsis* species *tetrahit* or a composition that contains it to stimulate hair growth or improve the appearance or hair fullness. The composition containing the plant extract is applied in both cosmetic and medical-trichological fields and can be applied topically on the scalp or administered orally.

10 Claims, 11 Drawing Sheets

VEGETABLE EXTRACT TO PREVENT AND TREAT HAIR LOSS

RELATED APPLICATIONS

This application is a national phase of International Application No. PCT/EP 2018/050656 filed on Jan. 11, 2018 and claims priority from Italian Patent Application No. 102017000003045 filed on Jan. 12, 2017, both incorporated by reference in their entirely.

FIELD OF THE INVENTION

The present invention relates to a composition containing a vegetable extract useful for preventing and treating hair loss.

The present invention originates in the field of the preparations of vegetable origin and products for trichological use.

In particular, the present invention relates to the use of a plant extract of a selected plant to stimulate hair growth, increase the fullness of the hair shaft and promote thickening of the scalp areas afflicted by thinning hair.

BACKGROUND

The piliferous structures physiology of the human body and the hair tropism study is object of numerous scientific studies. Notoriously, in the hair bulb life cycle follow each other the anagen (growth), catagen (involution) and telogen (rest) phases. To the hair growth period follows the regression phase, during which the deepest part of the follicle goes towards programmed cell death. Cycle starts again at the end of this phase. At the base of the growth cycle there is the ability of the hair bulb stem cells to come out, alternately, from a quiescence state.

During the bulb growth phase and hair production, proliferation, differentiation and survival activities regulated by growth factors predominate. The regression phase, instead, is characterized by the molecular pathways activation that induce apoptosis in the bulb cells. The physiological hair growth mechanism, however, with a certain frequency is subject to imbalance. A significant portion of the population, especially male, is in fact affected by problems of thinning or even premature loss of hair. From the available studies, it has emerged that the phenomena of early hair loss are due to a plurality of causes including a lack of nutrients, vitamins and minerals, hormonal imbalances, unregulation of local enzymatic systems and organism stress conditions.

In an attempt to remedy and prevent conditions that accelerate hair loss, trichological preparations have been formulated which, by acting on the scalp, nourishment, oxygenation and microcirculation, tend to improve conditions that contribute to physiological hair growth.

Among the products currently marketed in the trichological field, some are based on active substances of natural origin that locally act contributing to stimulate the hair bulb tropism and skin annexes.

The Applicant, being active in the preparation of the hair loss prevention products, has recently formulated a preparation for trichological use based on a plant extract obtained from the *Galeopsis segetum* Necker plant. The preparation is the object of the European patent application EP3062636A0. This European patent application documents how a plant extract belonging to the species *Galeopsis segetum* Necker carries out a satisfactory stimulation action of the hair follicle cells and a normalization of the piliferous structures life cycle phases.

The trichological activity of this plant extract, would seem to be attributable, at least in part, to some biologically active substances present in the extract from *Galeopsis segetum* Necker including the flavonoids hypolaetin 4'-methyl ether 7-(2"-allosyl)-glucoside monoacetylated, hypolaetin 4'-methyl ether 7-(2"-allosyl)-acetylated glucoside, isoscutellarin 7-(2"-allosyl) monoacetylated glucoside, hypolaetin 4'-methyl ether 7-(2"-allosyl) glucoside, hypolaetin 7-(2"-allosyl) monoacetylated glucoside, isoscutellarin 7-(2"-allosyl) glucoside and hypolaetin 7-(2"-allosyl) glucoside diacetylated.

As part of its experimentation activity, the Applicant has now found, in a totally unexpected way, that some samples containing extracts from species different from *Galeopsis segetum* Necker while containing the flavonoids previously referred to in marginal quantities, however, possess a biological and cellular antioxidant activity unexpectedly higher than expected.

Therefore, the Applicant found that this increased biological activity and cellular antioxidant activity are present in a plant extract from an accidental plant not belonging to the species *Galeopsis segetum* Necker object of the previous European patent application.

One of the aims of the invention therefore consists in providing a plant extract, different from the already known extract of *Galeopsis segetum* Necker, which is provided of an increased stimulation activity of the hair bulb cells proliferation and which therefore finds specific use in the trichological field. Another purpose of the invention is to provide a composition for stimulating hair growth based on plant extracts from a plant alternative to the species *Galeopsis segetum* Necker, the use of which is substantially free of side effects. Another purpose of the invention consists in to provide a composition for trichological use which can be applied locally or administered orally, the active ingredients of which originate from a plant of an alternative species to *Galeopsis segetum* Necker.

SUMMARY OF THE INVENTION

In the context of an experimentation activity carried out in its laboratories, the Applicant unexpectedly found that a plant extract obtained from *Galeopsis Tetrahit* L., an herbaceous plant belonging to the genus *Galeopsis*, possesses antioxidant and cell proliferation stimulation activities greater than those expected for other *Galeopsis* species such as *Galeopsis segetum* Necker.

Due to these increased activities, the extract from *Galeopsis Tetrahit* L. results in an improvement on the cell proliferation of the hair bulb and on the hair growth when compared to a *Galeopsis segetum* Necker extract.

The improvement of the trichological activity of the extract from *Galeopsis Tetrahit* L. over a *Galeopsis segetum* Necker extract, is surprising because both the species belong to the same plant genus and it was expected that both the species had same or very similar phytochemical composition.

According to a first aspect of the invention, the cosmetic use of a plant extract from the selected species *Galeopsis tetrahit* is therefore provided according to appended claim 1. In particular, the present invention provides the non-therapeutic or cosmetic use of a composition comprising a plant extract of *Galeopsis tetrahit* and a physiologically acceptable carrier for stimulating physiological hair growth, thickening hair or increasing hair volume in an individual.

According to a second aspect, the invention provides uses in the medical-trichological field of a plant extract of *Galeopsis tetrahit*, in particular in the treatment or prevention of androgenetic alopecia or of the defluvium telogenicum.

The invention therefore provides applications both in the cosmetic and therapeutic-trichological fields of the extract from *Galeopsis tetrahit* or a composition containing the extract.

Typically, the *Galeopsis tetrahit* extract or a composition containing the extract is suitable both for local application and for oral administration.

Therefore, the present invention originates from having surprisingly observed how the *Galeopsis tetrahit*, a selected species belonging to the genus *Galeopsis*, possesses biologically active components, some unidentified, which stimulate the hair bulbs cell proliferation allowing a use in the trichological field, for local application or oral administration of the extract.

Typically the composition of the invention contains a cosmetically or trichologically active amount of one or more biologically active components available in the *Galeopsis tetrahit* extract.

According to another aspect, the present invention relates to the cosmetic use of an extract combination from *Galeopsis tetrahit* and extracted from *Galeopsis segetum* Necker to stimulate the hair physiological growth and/or thicken the hair and/or increase the fullness of hair in an individual.

According to a further aspect, the present invention relates to a combination of extract from *Galeopsis tetrahit* and extract from *Galeopsis segetum* Necker for use in the treatment of androgenetic alopecia or defluvium.

BRIEF DESCRIPTION OF THE FIGURES

The features and advantages of the present invention will be more evident from the enclosed drawings, wherein.

DETAILED DESCRIPTION OF THE INVENTION

Figure 1:
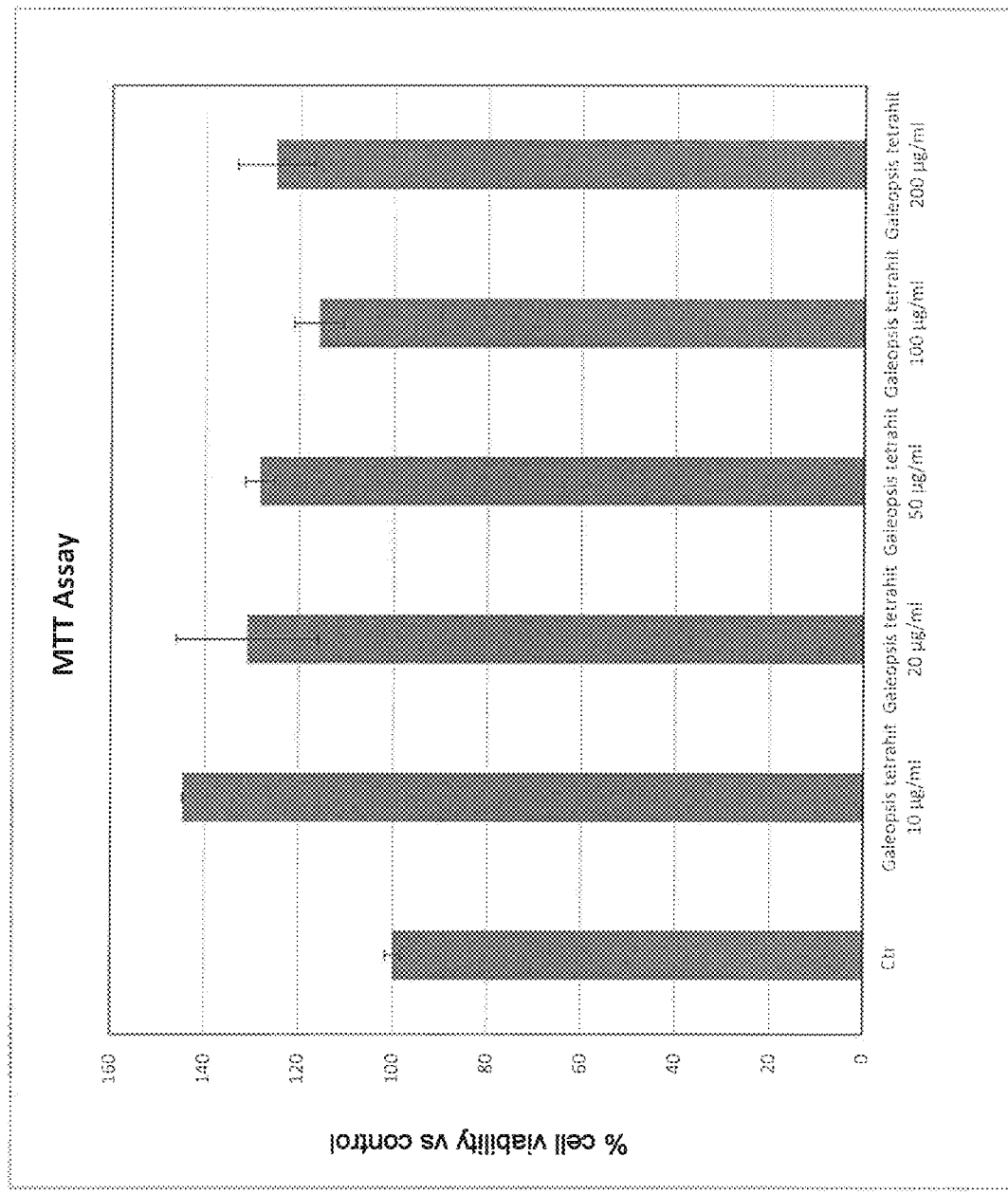
FIG. 1 shows bar graphs relating to a 24-hour MTT assay which illustrates the percentage of cell viability with respect to control determined by treatment with plant extracts containing increasing amounts of *Galeopsis tetrahit* according to Example 7.

The Applicant has found that a plant extract from the genus *Galeopsis*, species *Galeopsis tetrahit* contains biologically active components not fully yet identified that stimulate cell proliferation at the hair follicle level more intensively than other species of *Galeopsis*. The present invention includes applications both in the cosmetic field and in the medical-trichological field of the extract from the selected *Galeopsis* species according to the invention.

According to a first aspect, the invention relates to the cosmetic, non-therapeutic use of a plant extract from the genus *Galeopsis, tetrahit* species, to stimulate hair growth.

In particular, the invention relates to the cosmetic, non-therapeutic use of a plant extract from the genus *Galeopsis* species *Galeopsis tetrahit* to improve the appearance of the hair and/or to increase the fullness of the hair shaft.

According to a second aspect, the invention provides a plant extract of *Galeopsis tetrahit* for use in the treatment or prevention of androgenetic alopecia or defluvium telogenicum. According to other aspects, the invention relates to the cosmetic or therapeutic use in the trichological field of a combination of plant extracts from *Galeopsis tetrahit* and from *Galeopsis segetum* Necker.

Typically, the *Galeopsis tetrahit* plant extract according to the invention can be incorporated or formulated as a composition in both cosmetic and therapeutic applications.

The composition of the invention can be formulated for local application or for oral administration.

*Galeopsis tetrahit* L., also referred herein as *Galeopsis tetrahit*, a plant from which originates the extract at the basis of the invention, is a selected species of the genus *Galeopsis*.

Within the field of the invention, the plant extract can be obtained from any part of the *Galeopsis tetrahit* plant such as roots, leaves, fruits or even flowers. For the uses according to the invention, the extract is preferably obtained from the aerial part, typically the leaves, of the *Galeopsis tetrahit* plant.

According to some embodiments, the plant extract of the invention is obtained by extraction from a part of the plant or from a tissue thereof using a physiologically acceptable solvent as the extraction medium.

With the term of "physiologically acceptable solvent", it is meant a solvent that does not produce significant adverse reactions when introduced into the human body or applied to the human organism.

A suitable solvent to obtain the plant extract is a physiologically acceptable liquid in which at least some of the biologically active components of the selected plant are soluble and in which they do not undergo an alteration that deprives them of activity.

In some embodiments, the physiologically acceptable solvent is selected from water, ethanol, ethyl acetate and their mixtures. Typically, the solvent is a water/ethanol hydroalcoholic solution.

To obtain the plant extract of *Galeopsis tetrahit*, solid-liquid extraction techniques can be used to separate/extract one or more biologically active components from the plant's vegetable tissues.

In certain embodiments, the extraction of one or more biologically active components takes place by macerating a *Galeopsis tetrahit* vegetable portion or matrix in a suitable solvent, for example a hydroalcoholic mixture.

For example, a suitable extract can be obtained by dipping or macerating a portion of *Galeopsis tetrahit* plant aerial parts in a water-ethanol mixture, for a suitable time for enriching the solvent of one or more biologically active components. Under these conditions, the extraction of the biologically active components from the plant tissues of the selected plant takes place, substantially, by diffusion and/or osmosis. The maceration time of the plant portions in the solvent is variable, for example from 1 to 48 hours.

According to certain embodiments, the preparation of a suitable *Galeopsis tetrahit* extract comprises the following steps:
- shredding of dried aerial parts of the plant,
- addition of an extraction solvent such as a water ethanol mixture to obtain a hydroalcoholic drug/solvent ratio from about 1:10 to about 1:50 w/w,
- maceration of the aerial parts,
- extraction of biologically active components,
- filtration,
- concentration of the filtrate, for example, at reduced pressure by evaporation of the hydroalcoholic solvent,
- optional continuation of evaporation until solvent elimination
- optional drying of the extract.

In some embodiments, the extraction step can be repeated two or three times.

In the final step of solvent removal by evaporation, a solid support may optionally be added, such as, by way of non-limiting example, starches or maltodextrins, to obtain the extract in the form of dry powder.

According to another embodiment, the extraction method from *Galeopsis tetrahit* comprises the following steps:
- shredding, for example of the aerial parts of the plant
- transfer of the powder obtained in a suitable percolator
- percolation, for example, with a quantity of extraction solvent so as to have a drug/solvent ratio in weight from about 1:20 to about 1:100
- recirculation of the percolate part until exhaustion of the material to be extracted
- pressing of the extracted vegetable bed for the recovery of all the extraction solvent
- leachate filtration
- concentration of the filtrate, for example, at reduced pressure by evaporation of the solvent
- optional continuation of evaporation until solvent elimination
- optional drying of the extract.

According to some embodiments, in the final step of removing the solvent by evaporation a solid support is added, for example a starch or maltodextrin, to obtain the extract in the form of dry powder.

Typically, the extract obtained from *Galeopsis tetrahit* can be fluid, soft or dry. For example:
- in the fluid extract, 1 ml of extract contains biologically active components soluble in 1 g of vegetable drug;
- in the soft extract, the solvent is partially evaporated in particular until the extract not wets a filter paper;
- in the dry extract, the solvent is evaporated almost completely to obtain a powder.

It is possible to prepare extracts of *Galeopsis tetrahit* of different polarity.

For example, it is possible to obtain a high polarity extract using a polar solvent such as a hydroalcoholic solution, an intermediate polarity extract using a less polar solvent such as ethylacetate or an apolar extract using supercritical $CO_2$ with which it is possible to extract fractions of phytocomplexes that carry out inhibitory activity against the enzyme 5 alpha-reductase, type 2.

In certain embodiments, the extraction is carried out using a weight ratio between solvent and vegetable matrix ranging from 1:10 to 10:1.

It is possible to extract the biologically active plant components of *Galeopsis tetrahit* using alternative extraction techniques such as, for example, by digestion, infusion, squeezing, decoction, percolation, counter-current extraction, soxhlet, extraction with supercritical gases or ultrasounds.

The biologically active components extracted from *Galeopsis tetrahit* were not identified, however, it was found with in vitro tests that determine a cell proliferation action greater than that found with extracts from *Galeopsis segetum* Necker, under the same conditions of extraction.

The biologically active components contained in the plant extract of the invention reactivate the hair follicles life cycle also quiescent of the scalp. This activity has also been detected in the areas of scalp where the hair bulbs are partially atrophied, as in areas where there is a thinning hair.

The plant extract from the genus *Galeopsis* species *Galeopsis tetrahit* may be contained in a composition.

According to these aspects, the present invention therefore provides the cosmetic use of a composition comprising a plant extract from a plant belonging to the genus *Galeopsis* species *Galeopsis tetrahit* and a physiologically acceptable carrier in the treatment and/or prevention of hair loss or to stimulate growth physiological hair or to maintain a physiological hair tropism.

The Applicant has also observed that the extract of *Galeopsis tetrahit* possesses an action of inhibiting the enzyme 5 alpha-reductase in particular of type 2 which makes it useful for applications in the medical-trichological field as in the treatment or prevention of androgenetic alopecia and/o of the defluvium.

According to a fourth aspect, the invention relates to a composition comprising a *Galeopsis tetrahit* plant extract and a physiologically acceptable carrier for use in the treatment or prevention of androgenetic alopecia and/or in the defluvium. The composition of the invention proves effective in preventing and/or treating the forms of baldness or hair thinning, defluvium or androgenetic alopecia.

The composition of the invention can be formulated in a form for topical application or in a form for oral administration. Typically, the composition of the invention comprises a physiologically and/or pharmaceutically acceptable carrier, diluent or excipient.

The physiologically or pharmaceutically suitable carrier, diluent or excipient may be selected based on the route of administration for which the resulting pharmaceutical composition is intended. Any carrier and/or excipient suitable for the desired preparation form for administration is contemplated in the uses of the plant extract or active ingredients therein described therein.

Within the scope of the present invention, the term "carrier" refers to an excipient, vehicle, diluent or adjuvant, which may or may be present in the composition of the invention.

In some embodiments, the route of administration of the composition of the invention is the topical route. In these cases, the composition of the invention can be applied, in an effective quantity, directly on the scalp.

For example, in the treatment of hair loss or thinning forms a cosmetically/physiologically active amount of composition can be applied directly on the scalp, once or more times a day conveniently for cycles lasting 2-3 months, alternated with periods of absence of treatment. According to these aspects, the invention also relates to a cosmetic treatment method comprising the application on the scalp, or portion thereof, of an effective quantity of a composition according to one or more of the embodiments described and/or claimed therein. The composition for topical application may be in solid, semisolid or fluid form. Suitable formulations in solid form include creams, gels, ointments, pastes, unguents.

In other embodiments, the formulation for local administration is in fluid form, for example in the form of lotions, gels, shampoos, suspensions, emulsions.

In the case of fluid or semi-fluid formulations form, the plant extract can be diluted in a carrier in physiologically acceptable liquid form such as water, alcohol, hydroalcoholic or glyceric solution or mixed with other liquids suitable for local application.

By way of example, the compositions of the invention in liquid form can be prepared by dissolving the biologically active components of the extract in water and/or alcohol. The liquid composition can be buffered to reach a pH range conveniently selected from 5 to 7 to be compatible with the pH of the scalp and then filtered and packaged in suitable containers such as bottles or vials.

In some embodiments, the compositions of the invention may comprise excipients commonly used in the formulation of cosmetic or pharmaceutical preparations for local use, such as preservatives, bactericidal agents, stabilizers, emulsifiers, buffers, wetting, dyes and other excipients commonly used in preparation techniques.

In one embodiment, the formulation for the local application is in the form of an emulsion containing the extract carried in a suitable excipient. In some embodiments, the composition for topical application comprises an excipient of the hydroxymethylcellulose type and/or gelling with HLB suitable for the formulation and the substances.

According to other embodiments, the composition of the invention is in form for oral administration. In these cases, the composition contains the *Galeopsis tetrahit* extract as previously defined and one or more vehicles or excipients suitable for oral administration. By way of example, suitable excipients for oral administration include cellulose derivatives such as hydroxymethylcellulose, hydroxypropyl methylcellulose, methylcellulose, hydroxypropyl cellulose, hydroxyethyl cellulose, carboxyethyl cellulose, ethylhydroxyethyl cellulose, cellulose acetate butyrate, cellulose acetate phthalate, and mixtures thereof. Further examples of suitable excipients include the polymers belonging to the lactam family such as pyrrolidone and its derivatives, for example polyvinylpyrrolidone, polyvinylpolypyrrolidone and their mixtures, inorganic salts such as calcium or dicalcium phosphate, lubricants such as magnesium stearate, triacylglycerols and mixtures thereof. The compositions for oral administration may be in solid or liquid form. Typical solid form compositions include tablets, capsules, powders, granules, pills. Examples of compositions in liquid form include solutions, emulsions, suspensions, syrups. The compositions may also be in the controlled release form of the active components contained therein.

The tablets generally comprise a suitable carrier or excipient in which the plant extract is dispersed, typically in dry form.

The plant extract containing the biologically active components of the composition of the invention may be present in a variable amount, for example, from 0.0001% by weight to 10% by weight, typically from 0.1 to 5% by weight.

According to some embodiments, the composition of the invention further comprises one or more active substances such as vitamins, minerals, micronutrients and other substances active in stimulating the activity of the hair follicle.

The composition of the invention in the form for oral administration can be a medical device, a pharmaceutical formulation, or a dietary or nutritional supplement.

Nutraceutical product is a food product which may exert a physiological benefit or provides protection against a disadvantage or physiological disorder.

Dietary or food supplement means a product that may contain among others, a vitamin, mineral, plant extract, amino acid, metabolite, extract, concentrate or mixtures of these ingredients.

The amount administered and the frequency of composition administration will depend on the nature and severity of the trichological disease to be treated.

The present invention will now be described with reference to the following examples that are provided for illustration purposes only and are not to be intended as limiting the scope of the present invention.

Example 1

Tablet for Oral Use
Component Amount
*Galeopsis Tetrahit* dry extract 5-100 mg
Microcrystalline cellulose 200-300 mg
Silicon dioxide (colloidal silica) 2.5-10 mg
Magnesium stearate 2.5-10 mg
Polyethylene glycol 0.5-2.5 mg
Sodium alginate 0.025-0.5 mg
Hydroxy-propyl-methylcellulose 100-200 mg
Polyvinylpyrrolidone 0.5-1 mg
Copolymer of methacrylic acid 3.5-8.5 mg
Triethyl citrate 0.5-1 mg Example 2

Granular for Oral Use
Component Amount
Erythritol 20-30% w/w
*Galeopsis tetrahit* 0.2-3.5% w/w
Mannitol 39.7-6.2% w/w
Aroma 5-10% w/w
Sucralose 0.1-0.3% w/w
Starch 35-50% w/w Example 3

Pill for Oral Use
Component Amount
Caster sucrose 50-90 mg
*Galeopsis tetrahit* soft extract 5-100 mg
Microcrystalline cellulose 10-50 mg
Talc 10-20 mg
Corn starch 5-25 mg
Powdered sugar 5-15 mg
70% sorbitol not crystallizable 5-10 mg
Magnesium stearate 1-3 mg Arabic Gum 2-3 mg
Titanium Dioxide 1-2.5 mg
Gelatin 1-3 mg
Type A copolymer of methacrylic acid 1-2.5 mg
Light magnesium carbonate 0.5-1 mg
Polyethylene glycol 0.1-0.3 mg
Dibutylphthalate 0.1-0.25 mg
Triethyl citrate 0.002-0.05 mg
Methyl Paraxybenzoate 0.01-0.03 mg Example 4

Lotion for Application on Hair and Scalp
Component (INCI Name or Trade Name). Amount
Hydroxypropyltrimonium hyaluronate 0.05-0.1%
Type C denatured ethyl alcohol 5-20%
Lactic acid 0.1-0.3%
Meditanox H-10 0.001-0.002%
PEG-40 Hydrogenated castor oil 0.5-1.5%
Octadecyl di-t-butyl-4-hydroxyhydrocinnamate 0.02-0.06%
Lecithin NAT 8539 0.02-0.06%
Lypobelle soyaglycone 0.05-0.1%
Perfume Agrumes 2807/03 MOD.3/HICC FREE 0.1-0.2%
*Galeopsis Tetrahit* dry extract 0.05-1%
Fomblin HC/PU-CATS 0.005-0.02%
Water q.b. at 100%

Example 5

Treatment Shampoo
Component (INCI Name or Trade Name). Amount
Sulfetal LA B-E 2-4%
Pentavitin 0.5-1.5%
UCARE Polymer JR-400 0.5-1.5%
Amphotensid GB 2009 0.5-1.5%
Mirustyle MFP PE-LQ-(WD) 0.25-0.75%
Tetrasodium ethylenediaminetetraacetate 0.2-0.6%
Antil 127 0.1-0.3%
Oxetal VD 92 0.05-0.3%
Citric acid monohydrate 0.25-1%
Sodium hydroxymethylglycinate 0.4-1.6%
PEG-8 caprylic/capric glycerides 0.25-1%
*Galeopsis tetrahit* dry extract 0.0025-1%
BHA 0.005-0.02%
Di-PPG-2 Myreth-10 Adipate 1.25-5%
Dimethicone PEG-7 Isostearate 0.25-1%
Water q.b. at 100%

Example 6

Skin Emulsion
Component Amount
Propylene glycol 6-8%
Glyceryl stearate palmitate 3-5%
Coconut oil 2-4%
Cetostearyl alcohol 1-3%
Emulsifying wax 1-3%
Benzyl alcohol 0.5-1.5%
*Galeopsis tetrahit* soft extract 0.5-2%
Cetyl alcohol 0.25-1%
Water q.b. at 100%

Example 7

Comparative Test
Comparative Study In Vitro on *Galeopsis segetum* and *Galeopsis tetrahit*
Purpose of the Test
The experimental procedure described below concerns a comparative study of the in vitro activity of plant extracts of *Galeopsis segetum* and *Galeopsis tetrahit*, in order to characterize its antioxidant activity as a function of the stimulation activity of hair growth.
Materials
Tested Samples

| Internal Name | GB | GE | TB | TE |
|---|---|---|---|---|
| Unique name identifier | Plant biomass of *Galeopsis segetum* | Hydro-alcoholic dry extract of *Galeopsis segetum* | Plant biomass of *Galeopsis tetrahit* | Hydro-alcoholic dry extract of *Galeopsis tetrahit* |
| Lot | Lot C/181286 | Lot 921/30/D | Lot C/203285 | Lot 994/39/A |
| Storage | T.A. | T.A. | T.A. | T.A. |

All extracts were diluted 50 mg/ml in DMSO and sterile filtered.
The stock solutions have been stored at −20° C.
Samples Solubility Indications
VEGETABLE BIOMASS (*Galeopsis segetum* and *Galeopsis tetrahit*). Finely minced with pestle and grinder. Diluted in 100% DMSO does not reach full solubility. Sonicated 15 minutes at RT, greater dispersion. The 5 mg/ml solution in DMEM is dispersible. The 1 mg/ml solution is completely soluble and it is filtered by a filter with 0.22 μm mesh;
DRY HYDRO-ALCOHOLIC SAMPLE (*Galeopsis segetum* and *Galeopsis tetrahit*): diluted in 100% DMSO, it reaches full solubility. Sonicated 15 min at RT. The 5 mg/ml solution in DMEM is dispersible. The 1 mg/ml solution is completely soluble and it is filtered by 0.22 μm mesh;
Used Reagents and Instrumentation

| REAGENTS | SUPPLIER |
|---|---|
| Hydrogen peroxide 30% | SIGMA, 216763 |
| Agarose (For routine use) | SIGMA, A9539-100G |
| Calf Bovine Serum | ATCC, 30-2030 |
| 2',7'-dichloro-fluorescein acetate | SIGMA, 35845 |
| Dimethylsulfoxide | SIGMA, D2438-50ML |
| Dulbecco'sModifiedEagle's Medium | ATCC, 30-2002-500ml |
| Dulbecco'sPhosphateBuffered Saline | SIGMA, D8537 |
| Gelred nucleic acid gel stain 10000x in water-0.5 ml | Diatech Labline, 41003 |
| Gel Loading Buffer | SIGMA, G2526 |
| RNAse, none detected | |
| PRIME SCRIPT RT reagent kit (Perfect Real time) 200 rxn | TAKARA, RR037A |
| MTT | SIGMA-Aldrich, M2128 |
| Penicillin-Streptomycin | SIGMA, P0781 |
| PreMix Ex Taq | TAKARA, RR039A |
| TaqMan ® Gene Expression Assays for SRD5A1 Mm00614213ml | APPLIED BYOSISTEMS, 4331182 |
| TaqMan ® Gene Expression Assays for SRD5A2 Mm00446421ml | APPLIED BYOSISTEMS, 4331182 |
| TaqMan ® Gene Expression Assays for βactina Mm00466519ml | APPLIED BYOSISTEMS, 4331182 |

| REAGENTS | SUPPLIER |
|---|---|
| Testosterone | SIGMA, 86500 |
| Trypsin-EDTA solution | SIGMA, T3924 |
| α-tocopherol | SIGMA, T3251 |
| Tri reagent Solution | Thermo Fisher, AM9738 |
| Chloroform | SIGMA, 366919-1L |
| Isopropanol | SIGMA, I9516-500 ml |
| Cellytic M | SIGMA, C2978 |
| ProteaseInhibitor Cocktail | SIGMA, T1500 |

| INSTRUMENTATION | SUPPLIER |
|---|---|
| Spectrophotometer (MOD: 6715, BS-6715B0) | Jenway UV/VIS |
| 15 L digital water bath from +5° C. to +100° C. (Mod: Swbd1, BS-SWB2D) | Stuart |
| Balance (Mod. XS204) | Mettler Toledo |
| Laminar flow cabinet (Mod: Gemini) + UV lamp with anti-reflex equipment | SterilManifacturingDivision |
| HeraCell $CO_2$ incubator (Mod: 150 ADV) | ThermoScientific |
| 85° C. horizontal freezer ULT130, 120 L (Mod: Labfrost, MME-TE21140) | Elcold |
| Bürker counting chamber w/clamps (DI-DA-443/3) | Carlo Erba |
| Microplateautoreader (EL 808) | Biotek |
| Vortex | Arhos160-PBI International |
| FluoroskanAscent FL MicroplateFluorescence Reader | Thermo Fisher Scientific Inc., Waltham, MA |

Used Biological Models

Cultured Embryonic Fibroblast Cultures

The immortalized line of murine embryonic fibroblasts BALB/c3T3, Clone A31 (ATCC, Manassas, Va., USA) was obtained from National Institute for Cancer Research (Genova, Italy).

Cells were cultured in 25 $cm^3$ sterile flasks and incubated at 37° C. in a 5% $CO_2$ humid atmosphere. DMEM was used as culture medium (Dulbecco's Modified Eagle's Medium, ATCC, Manassas, Va., USA) added to 10% of fetal bovine serum (FCS), 1% of non-essential amino acids (NEAA), 1% of a mixture of penicillin and streptomycin (Pen-Strep Mix). These last reagents were all purchased by Lonza Inc. (Barcelona, Spain)

During culture, the 1:3 split was performed every 2 days, at 80% confluence, by washing with 1×PBS (Lonza, Barcelona, Spain) and cell separation with a trypsin-EDTA solution (Lonza, Barcelona, Spain) at 37° C. for 2 minutes.

| ICLC CATALOG CODE | CCL-163 ™ |
|---|---|
| DEPOSITOR | Aaronson S. |
| BIBLIOGRAPHIC REFERENCES | 10993-5: 1999. Aaronson S A, Todaro G J. Development of 3T3-like lines from Balb-c mouse embryo cultures: transformation susceptibility to SV40. J. Cell. Physiol. 72: 141-148, 1968. PubMed: 4301006
Todaro G J, Aaronson S A. Properties of clonal lines of murine sarcoma virus transformed Balb-3T3 cells. Virology 38: 174-202, 1969. PubMed: 4306523
Aaronson S A, Todaro G J. Basis for the acquisition of malignant potential by mouse cells cultivated in vitro. Science 162: 1024-1026, 1968. PubMed: 4301647
Jainchill J L, Todaro G J. Stimulation of cell growth in vitro by serum with and without growth factor. Relation to contact inhibition and viral transformation. Exp. Cell Res. 59: 137-146, 1970. PubMed: 4194429
Thompson S A, et al. COOH-terminal extended recombinant amphiregulin with bioactivity comparable with naturally derived growth factor. J. Biol. Chem. 271: 17927-17931, 1996. PubMed: 8663535
Anderson M T, et al. Simultaneous fluorescence-activated cell sorter analysis of two distinct transcriptional elements within a single cell using engineered green fluorescent proteins. Proc. Natl. Acad. Sci. USA 93: 8508-8511, 1996. PubMed: 8710900
Biological evaluation of medical devices. Part 5: Tests for in vitro cytotoxicity. Sydney, NSW, Australia: Standards Australia; Standards Australia AS ISO 10993.5-2002.
Biological evaluation of medical devices-Part 5: Tests for in vitro cytotoxicity. Geneva (Switzerland): International Organization for Standardization/ANSI; ISO ISO |

Controls

MTT Assay (BALB3T3)

POSITIVE CONTROL: Cells not treated in DMEM medium (Dulbecco's Modified Eagle's Medium, ATCC, Manassas, Va., USA) with 10% fetal bovine serum (FCS), 1% of non-essential amino acids (NEAA), 1% of a mixture of penicillin and streptomycin (Pen-Strep Mix), and maintained in culture plates (96 well) from 25 $cm^2$ to 37° C. and 5% $CO_2$.

DCFH-DA Assay and MTT-Induced Oxidative Stress Test (BALB3T3)

NEGATIVE CONTROL: Cells not treated in DMEM medium (Dulbecco's Modified Eagle's Medium, ATCC, Manassas, Va., USA) added to 2.5% of fetal bovine serum (FCS), 1% of non-essential amino acids (NEAA), 1% of a mixture of penicillin and streptomycin (Pen-Strep Mix), and maintained in culture plates (96 well) from 25 $cm^2$ at 37° C. and 5% $CO_2$ (in the dark).

POSITIVE CONTROL: Cells treated for 2 h with 1 mM hydrogen peroxide in DMEM medium (Dulbecco's Modified Eagle's Medium, ATCC, Manassas, Va., USA) added to 2.5% of fetal bovine serum (FCS), 1% of non-essential amino acids (NEAA), 1% of a mixture of penicillin and streptomycin (Pen-Strep Mix), and maintained in culture plates (96 well) from 25 $cm^2$ at 37° C. and 5% $CO_2$ (in the dark).

5-Alfa Reduttasi Modulation Study (BALB3T3)

NEGATIVE CONTROL: Cells not treated in DMEM medium (Dulbecco's Modified Eagle's Medium, ATCC, Manassas, Va., USA) added to 10% of fetal bovine serum (FCS), 1% of non-essential amino acids (NEAA), 1% of a mixture of penicillin and streptomycin (Pen-Strep Mix) and Testosterone 10 ng/mL, and maintained in culture plates (12 well) from 25 $cm^2$ at 37° C. and 5% $CO_2$.

POSITIVE CONTROL: Cells treated for 24 h with finasteride (0.05 mg/ml) in DMEM medium (Dulbecco's Modified Eagle's Medium, ATCC, Manassas, Va., USA) added to 10% of fetal bovine serum (FCS), 1% of non-amino acids Essential oils (NEAA), 1% of a mixture of penicillin and streptomycin (Pen-Strep Mix) and Testosterone 10 ng/ml, and maintained inputting plates (12 well) of culture from 25 $cm^2$ at 37° C. and 5% $CO_2$.

Methods

Preliminary Cytotoxicity Test (MTT Assay)-BALB3T3

Method Principles

The MTT assay 3-(4,5-dimethylthiazol-2-yl)-2,5-diphenyltetrazolium bromide is a colorimetric assay used to assess cell proliferation in vitro, as it allows to measure cell proliferation and vitality through the evaluation of mitochondrial activity. This method is very useful to measuring cell growth following treatment with mitogenic agents, antigenic stimuli, growth factors and for cytotoxicity studies.

The test involves the use of a chromogenic oxidizing agent, MTT, consisting of a polycyclic system ($C_{18}H_{16}BrN_5S$) equipped with a tetrazolium ring that can be easily reduced by mitochondrial dehydrogenases or other electronic transport systems, forming, for the opening of the tetrazolium ring, a nitrogenous chromogenic compound known as formazan. Formazan forms insoluble crystals in the intracellular environment, to which the membranes are, substantially, impermeable: the entry of the molecule into the cell is therefore permitted, but not the product exit, if it has been correctly metabolized, that is, if the electronic transport chains are still metabolically active.

Formazan crystals are subsequently solubilized in dimethylsulfoxide (DMSO), thus determining the solution color change from yellow to dark blue-violet.

Experimental Procedure

The assay was conducted following the Mosmann method (1983), with some minor modifications. BALB3T3 cells were seeded at a density of $5*10^4$ cells/well in 96-well plates. After 24 hours, reaching a confluence of about 80%, the cells were treated with 6 increasing concentrations of *Galeopsis segetum* and *Galeopsis tetrahit* extracts (vegetable biomass and dry hydro-alcoholic sample) 10-20-50-100-200 mg/ml in complete medium. Control cells, instead, were kept in culture in complete medium.

The plates were incubated at 37° C., at 5% $CO_2$ for 24, 48 and 72 hours. At the end of all treatments, the medium was collected and replaced with 100 µl of a solution of MTT (Sigma-Aldrich, St. Louis, Mo., USA) 0.5 mg/ml in complete culture medium.

After 3 hours incubation at 37° C., the medium was taken and the formazan crystals were solubilized with 100 µl per well of DMSO (Sigma-Aldrich, St. Louis, Mo., USA). The plate, covered with aluminum, was placed on a mechanical stirrer (Arhos 160—PBI International, Milan, Italy) at 120 rpm for 15 minutes at room temperature.

The colored solution absorbance was measured by a spectrophotometric microplate reader (BioTek Instruments Inc., Bad Friedrichshall, Germany) at a 570 nm wavelength (reference wavelength at 630 nm).

The data were expressed as a percentage of cell viability with respect to control cells (ctr), according to the following formula:

% cell viability/*ctr*=(Sample Abs/*ctr* Abs)*100

All analysis were performed at least twice using duplicate samples.

MTT with Induced Oxidative Stress-BALB3T3
Method Principles

BALB3T3 mouse fibroblasts are one of the validated models for studies of oxidative stress in vitro (Subirade et al., 1995; Kutuk et al., 2004).

Studies conducted in 2005 by Rajapakse and coworkers (2005) highlighted the possibility of exploiting a highly used and versatile method such as that of the MTT assay for the in vitro study antioxidant activity of active compounds. Specifically, through this method it is possible to study the protective effects of these compounds on cells subsequently subjected to oxidative stress. The induction of oxidative stress is carried out by incubation with hydrogen peroxide, an agent that induces the production of oxidative damage in the cells through ROS formation. The possible protective effects can be determined through the assessment of cell viability after oxidative stress of the pre-treated/pre-exposed cells to the active compounds to be tested, in comparison with cells subjected to the same oxidative stress. A greater cell viability will correspond to a protective effect of the tested compounds.

Experimental Procedure

The assay was conducted according to the method described by Coda and coworkers (Coda et al., 2012), with some modifications.

BALB3T3 murine fibroblasts were seeded in a 96-well plate at a density of $5*10^4$ cells/well and incubated at 37° C., at 5% $CO_2$, up to about 80% confluence.

Subsequently, the cells were incubated for 16 hours with *Galeopsis segetum* and *Galeopsis tetrahit* (plant biomass and dry hydro-alcoholic sample) at concentration 50 µg/ml.

The dilutions were prepared from 1000× stocks in DMSO, sterile filtered and using DMEM medium supplemented with 2.5% fetal bovine serum (FCS), 1% non-essential amino acids (NEAA), 1% of a penicillin mixture and streptomycin (Pen-Strep Mix).

Cells treated with 1 mM $H_2O_2$ were used as a positive control; cells maintained in culture medium alone (DMEM 2.5% FCS) were, instead, used as a negative control.

At the end of the 16 hours of pretreatment, the cells were washed with PBS 1× and incubated for 90 minutes with a 1 mM solution of $H_2O_2$ (Sigma-Aldrich, St. Louis, Mo., USA) in medium without serum, in the dark, at 37° C. and 5% of $CO_2$.

Once the oxidation stress induction phase was completed, the cell viability of the various samples was evaluated, according to the method described in point 4.1.2 (assay with MTT).

The data were expressed as a percentage of cell viability compared to non-stressed control cells (ctr), according to the following formula:

% cell viability/*ctr*=(Sample Abs/*ctr* Abs)*100

All analysis were performed at least twice using duplicate samples.

Study of the Effects of *Galeopsis segetum* and *Galeopsis tetrahit* and on ROS Production Using a DCFH-DA-BALB3T3 Assay Method Principles The ROS production in the BALB3T3 murine fibroblast cell line was determined by spectrophotometer using the 2,7-dichlorofluorescein-diacetate (DCFH-DA) assay, as described by Tobi et al. (Tobi et al., 2000).

DCFH-DA is a non-fluorescent compound in lipophilic form, able to spread through the cell membrane. Once inside the cell, it is deacetylated by the intracellular esterases to reduced 2,7-dichlorofluorescein (DCFH), which is also non-fluorescent. DCFH, unable to cross again the cell membrane, eventually ends up accumulating in the cells (Curtin et al., 2002). The intracellular ROS reaction leads to the oxidation of 2.7-dichlorofluorescein (DCF) DCFH, a highly fluorescent compound. This fluorescence intensity can be detected with a fluorimeter, allowing estimating the amount of ROS produced in the cells.

Figure 5:
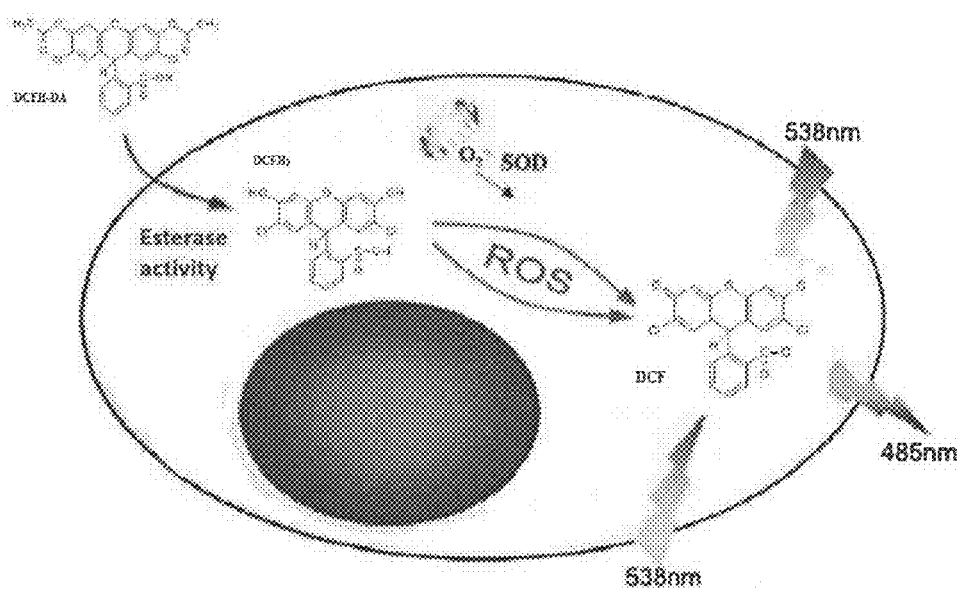
FIG. 5 shows a diagrammatic representation of the principle of the test with dichlorofluorescein of Example 7.

FIG. 5 shows a schematic representation of the dichlorofluorescein assay principle: the DCF non-fluorescent precursor enters the cell, it is deacetylated and subsequently oxidized, in case of increased ROS presence in cell, to give the DCF fluorophore. This can be excited at 538 nm, by spectrofluorimeter and emits fluorescence at 485 nm.

Experimental Procedure

The protocol used for this experiment represents a modified version of the one described in a work by Tobi and coworkers (Tobi et al., 2000).

BALB3T3 murine fibroblasts were seeded in 96-well plates at a density of $5*10^4$ cells/well and incubated until about 80% confluence was achieved.

Subsequently, the cells were incubated for 16 hours with *Galeopsis segetum* and *Galeopsis tetrahit* (plant biomass and dry hydro-alcoholic sample) at a concentration of 20 µg/ml. The dilutions were prepared from 1000× stock in DMSO, sterile filtered and using DMEM medium supplemented with 2.5% fetal bovine serum (FCS), 1% non-essential amino acids (NEAA), 1% of a penicillin mixture and streptomycin (Pen-Strep Mix).

Cells treated with 1 mM $H_2O_2$ were used as a positive control; cells maintained in culture medium alone (DMEM 2.5% FCS) were used instead as a negative control.

α-Tocopherol, was tested at a concentration of 25-50-250-500 µM.

At the end of the incubation, oxidative stress was induced, by treatment of 90 minutes with a 1 mM solution of $H_2O_2$, in the dark, at 37° C. and 5% of $CO_2$.

Once the treatment was complete, the cells were washed twice with 1×PBS and lysed with CelLytic™ lysis buffer (Sigma-Aldrich, St. Louis, Mo., USA) according to the supplier's protocol.

Subsequently, the lysates were transferred in a 96-well black plate and the fluorescence of DCF was read spectrofluorimetrically using a FluoroskanAscent FL Microplate Fluorescence Reader (Thermo Fisher ScientificInc., Waltham, Mass., USA), with excitation and emission wavelengths of 485 and 538 nm respectively.

The emission values (RFU) obtained for each sample, related to the production of intracellular ROS, were compared to the emission value obtained for the negative control (control, cells treated with 1 mM $H_2O_2$) and expressed as a percentage of ROS produced according to the following equation:

$$\% \text{ ROS products}/ctr = (Abs538 \text{ nm sample}/Abs538 \text{ nm } ctr)*100$$

All analyzes were performed at least twice using duplicate samples.

Effects of *Galeopsis segetum* and *Galeopsis tetrahit* Study on the Activity of 5 Alpha-Reductase (Isoform 2)-BALB3T3

Experimental Procedure

The gene expression of the isoform 2 of 5 alpha-reductase (SRD5A2) in BALB3T3 cells was evaluated by relative quantitative RT-PCR (quantitative reverse transcription polymerase chain reaction-qRT-PCR).

This analysis has foreseen 3 sequential phases:
Total RNA extraction;
Reverse transcription in cDNA;
qRT-PCR.

BALB3T3 murine fibroblasts were seeded in 12-well plates at a density of $0.5*10^6$ cells/well and incubated until about 80% confluence was achieved.

Subsequently, the cells were incubated for 24 hours with *Galeopsis segetum* and *Galeopsis tetrahit* (vegetable biomass and dry hydro-alcoholic sample) at the following concentrations: 20-50 and 100 µg/ml.

The dilutions were prepared from 1000× stocks in DMSO, sterile filtered and using DMEM medium added to 10% of fetal bovine serum (FCS), 1% of non-essential amino acids (NEAA), 1% of a mixture of penicillin and streptomycin (Pen-Strep Mix).

Cells maintained in culture medium alone (DMEM 2.5% FCS) were used instead as a negative control.

Finasteride, a selective inhibitor of the 5 alpha-reductase isoform 2 (SRD5A2), was tested at a concentration of 0.05 mg/ml.

At the end of the incubation, the RNA was extracted,

Total RNA was extracted from BALB3T3 cells using TriReagent (Sigma Aldrich) according to the procedure described by Chomczynski and Mackey (1995).

At the end of the incubation with the active compounds of interest, cells were washed with PBS (1×) and finally subjected to the RNA extraction procedure. At the end of the extraction, using a spectrophotometer (Jenway UV/VIS MOD: 6715, BS-6715B0), the concentrations in µg/ml of total RNA extracted at the wavelength of 260 nm were calculated. Finally, the integrity of RNA (2 µg/ml) by electrophoretic run on 1% agarose gel was evaluated.

Total RNA was converted into cDNA (complementary DNA), using an enzyme capable of synthesizing a DNA molecule using an RNA strand as a template; this DNA polymerase-dependent RNA enzyme, is called reverse transcriptase.

It binds to the 3' end of a single RNA strand and through the random primers and deoxynucleotide triphosphates (DNTP) synthesizes the cDNA strand.

For this purpose a commercial kit "PrimeScript™ RT Reagent Kit (perfect Real Time)" was used (TakaraBioInc., Japan) containing 5× PrimeScript Buffer (for real Time); PrimeScript RT Enzyme Mix1; OligodTPrimer; Random examers; RNAse free $dH_2O$.

The extracted and quantified RNA was diluted to a concentration of 2 µg/ml and retro-transcripted in cDNA. A 10 µl Master Mix was prepared (containing 5× PrimeScript Buffers (for real time), PrimeScript RT Enzyme Mix1, OligodTPrimer 50 µM, Random examers 100 µM) to which 10 µl of RNA (2 µg/ml) were added.

The samples were placed in a thermocycler (Stratagene Mx3000P Real Time PCR System, Agilent Technologies Italy S.p.A., Milan, Italy) and subjected to retro-transcription under the following conditions:
37° C. for 15 minutes;
85° C. for 5 seconds;
4° C. hold.

At the end of the retro-transcription to the samples 30 µl of DEPC water were added to obtain a final concentration of cDNA of 40 ng/µl.

QRT-PCR represents a method of amplification and quantification in real time of the amplifiers produced by monitoring the fluorescence emitted during the reaction.

For the RT-PCR amplification, the TaqMan® probe system (AppliedBiosystems) was used. The following TaqMan probes were used: Mm00446421 ml (SDR5A2) and Mm00466519 ml (β-actin). β-actin was used as the control gene (housekeeping).

The Taqman probe is a type of probe that allows the development of fluorescence during amplification. At its 5'-end a reporter (fluorophore FAM™), while at the 3'-end a quencher are bound. The proximity between the reporter and the quencher cancels the emission of the fluorescence signal. Only with the 5' exonuclease activity of the thermostable DNA polymerase (Taq polymerase) is detected fluorescence and the accumulation of amplification products can be evaluated by increasing the fluorescence of the reporter which increases with each cycle.

For the qRT-PCR a Master Mix has been set up as follows:
10 µl "2× Premix Ex Taq";
1 µl "20× TaqMan Gene ExpressionAssays" (containing 2 primers and the fluorescent probe labeled with FAM™ fluorophore);
0.4 µl passive reference Rox II;
5 µl DEPC water.

To the Master Mix 4 µl of cDNA were added for the target gene and 1 µl of cDNA for the housekeeping gene.

The amplification was conducted for 40 cycles under the following conditions:
95° C., 30 seconds (AmpliTaq activation);
95° C., 5 seconds (Denaturation)
60° C., 20 seconds (Annealing—extension);
Each analysis was conducted in duplicate.

The obtained data were analyzed according to the $2^{-\Delta\Delta Ct}$ method and it was thus possible to calculate the relative expression values of the gene of interest, normalized with respect to the housekeeping gene and calibrated on the control sample (untreated cells):

$$\Delta\Delta Ct = \Delta Ct_{target-housekeeping}(\text{control}) - \Delta Ct_{target-housekeeping}(\text{treated cells})$$

Assuming a 100% amplification efficiency, the $2^{-\Delta\Delta Ct}$ was calculated.

Results
Preliminary cytotoxicity assay (MTT assay)-BALB3T3

TABLE 1

| Substances | % vitality-Mean 24 h | std err |
|---|---|---|
| Ctr | 100 | 1.58 |
| Galeopsis tetrahit 10 µg/ml | 144.70 | 0.05 |
| Galeopsis tetrahit 20 µg/ml | 131.02 | 15.04 |
| Galeopsis tetrahit 50 µg/ml | 128.33 | 3.12 |
| Galeopsis tetrahit 100 µg/ml | 115.94 | 5.19 |
| Galeopsis tetrahit 200 µg/ml | 125.07 | 8.12 |

FIG. 1 includes the data obtained from the MTT assay (mean±SE).

The results show how Galeopsis tetrahit exerts a significant stimulus to cell proliferative activity at all concentrations studied and reported in Table 1 above. This is a desirable effect within the scope of the hair physiology action.

ROS Intracellular Production (DCFH-DA assay)-BALB3T3

TABLE 2

| Substances | % ROS | std err |
|---|---|---|
| ctr + $H_2O_2$ | 100 | 25.26 |
| α-tocopherol 25 µM | 39.67 | 4.38 |
| Galeopsis segetum 20 µg/mL | 42.37 | 0.84 |
| Galeopsis tetrahit 20 µg/mL | 28.26 | 3.95 |

Figure 2:
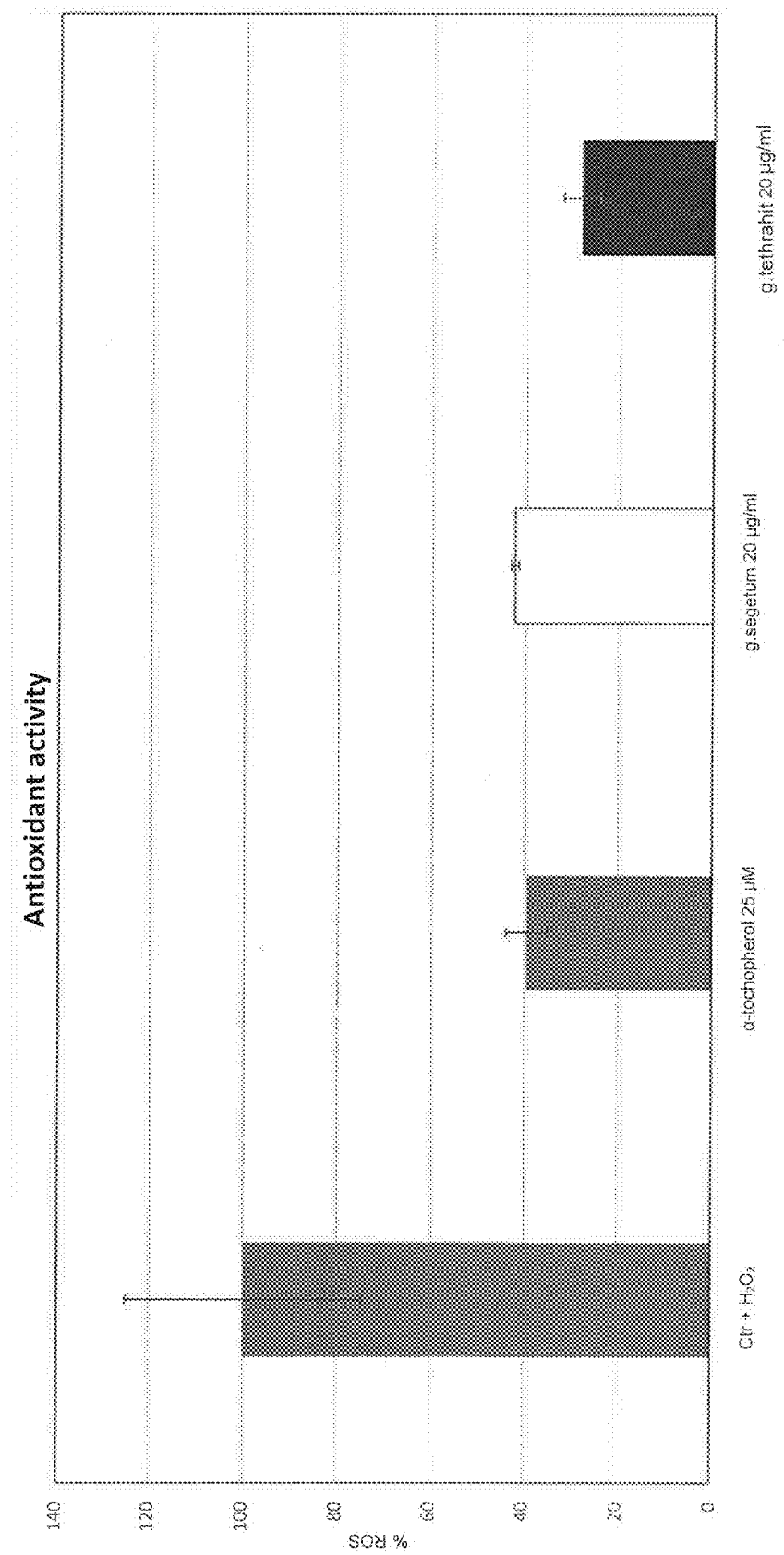
FIG. 2 shows bar graphs representative of antioxidant activity comparative data expressed as a ROS percentage of *Galeopsis segetum* and *Galeopsis tetrahit* extracts, as described in Example 7.

FIG. 2 attached to the present application, reports the antioxidant activity of both Galeopsis segetum and Galeopsis tetrahit. Table 2 above shows the scavenger activity data.

The results show how the extracts express a strong antioxidant activity, also in comparison with the 25 µM α-tocopherol.

While Galeopsis segetum has a comparable activity to alpha-tocopherol, used as a reference standard for scavenging, Galeopsis tetrahit has a significantly better activity than alpha-tocopherol.

Galeopsis tetrahit also demonstrated, with the same concentration, an almost double activity compared to that of Galeopsis segetum.

Effects of Galeopsis segetum and Galeopsis tetrahit Extracts Study on Induced Oxidative Stress-BALB3T3

TABLE 3

| Substances | % cells viability | std err |
|---|---|---|
| Ctr | 100 | 3.66 |
| Ctr + $H_2O_2$ | 58.43 | 4.08 |
| α-tocopherol 50 µM | 78.37 | 1.02 |
| Galeopsis segetum 50 µg/mL | 75.95 | 7.02 |
| Galeopsis tetrahit 50 µg/mL | 91.57 | 4.08 |

Figure 3:
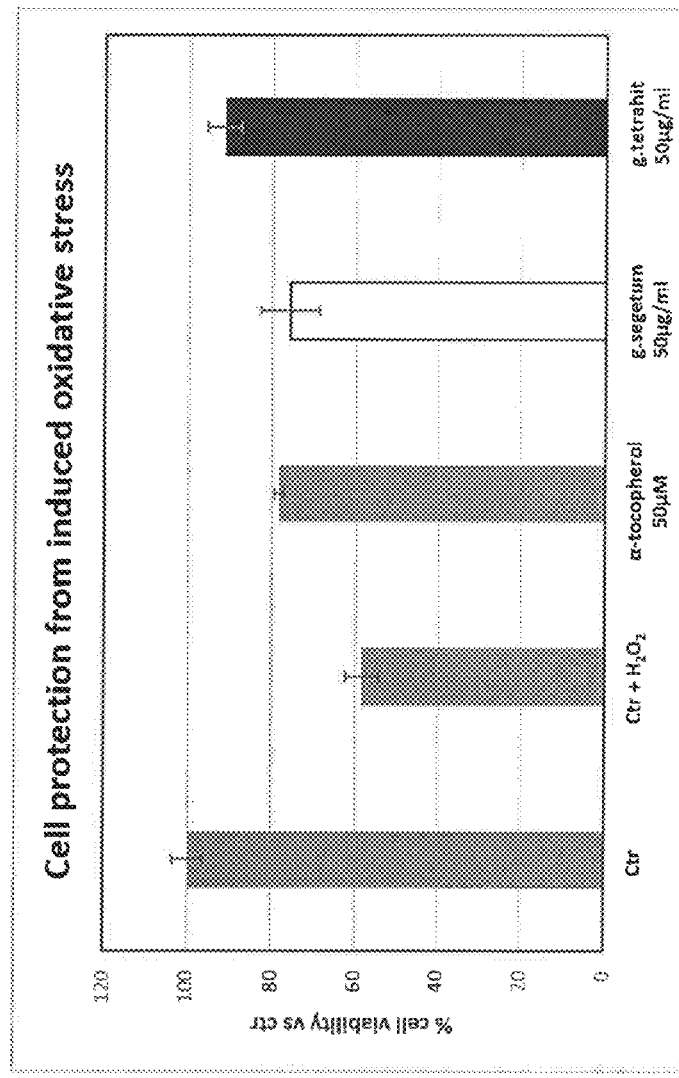
FIG. 3 shows bar graphs representative of cell protection activity against oxidative stress induced by $H_2O_2$.

FIG. 3 enclosed here shows the data for cell protection activity against oxidative stress induced by $H_2O_2$.

Induced oxidative stress produces a situation of cellular suffering that results in a significant cell population loss. Treatment with Galeopsis segetum and Galeopsis tetrahit shows a protective ability against the apoptotic process induced by oxidative stress.

Also in this experiment, alpha-tocopherol was used as reference standard for the protection against oxidative stress.

Galeopsis segetum shown an activity comparable to alpha-tocopherol whereas Galeopsis tetrahit shown a significantly better activity than both alpha-tocopherol and Galeopsis segetum.

Effects of Galeopsis segetum and Galeopsis tetrahit Study on the Activity of 5 Alpha-Reductase (Isoform 2)-BALB3T3

| Substances | mRNA SERD5A2 | std err |
|---|---|---|
| Ctr | 1 | 0.1 |
| finasteride 0.05 mg/mL | 0.31 | 0.041 |
| Galeopsis segetum 50 µg/mL | 0.52 | 0.038 |
| Galeopsis tetrahit 50 µg/mL | 0.58 | 0.108 |

Figure 4:
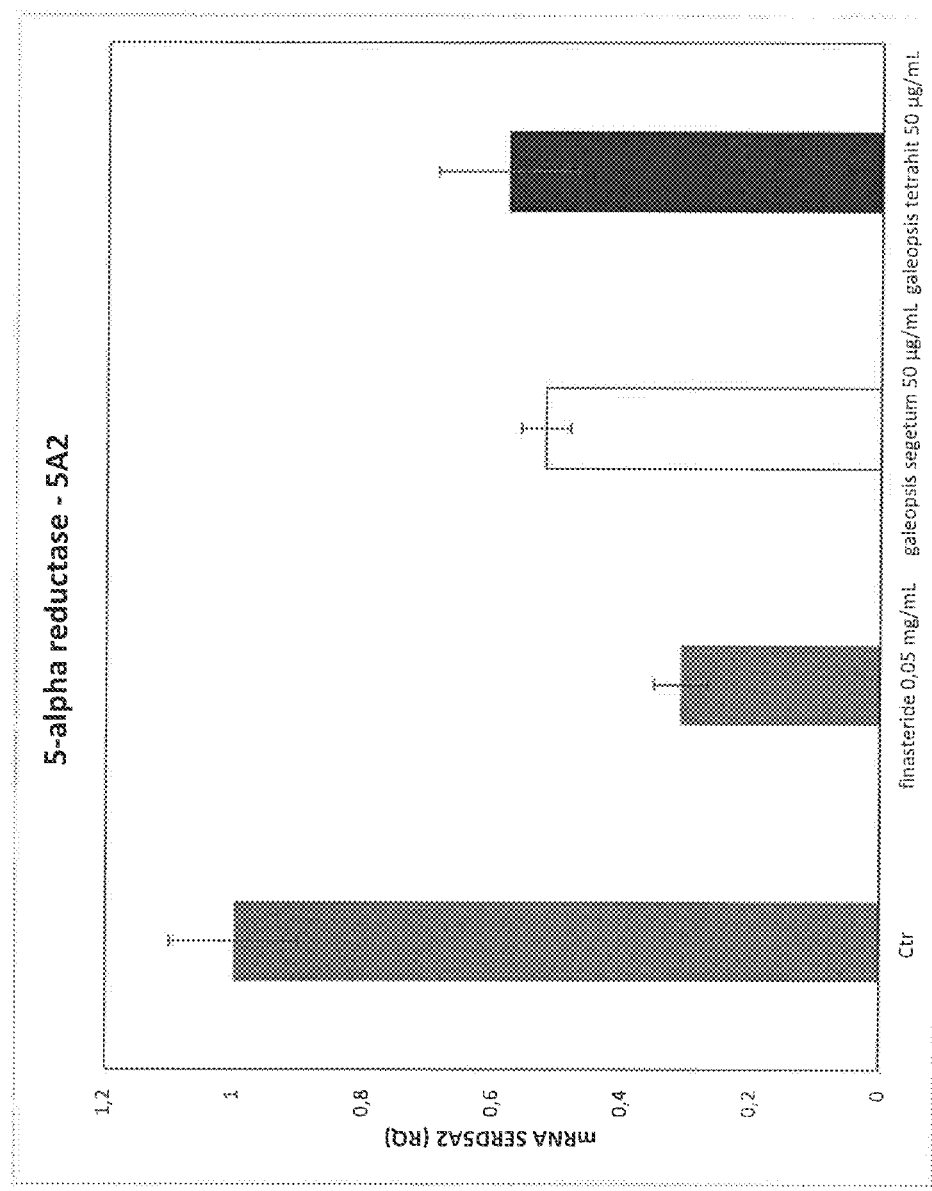
FIG. 4 shows bar graphs representative of the effects on the 5 alpha-reductase isoform 2 activity, of samples of finasteride, and hydroalcoholic extracts of *Galeopsis segetum* and *Galeopsis tetrahit* of the invention, as reported in Example 7.

FIG. 4 illustrates the gene expression data of the 5 alpha-reductase isoform 2, target of the Finasteride drug, which has been used as a comparison. Even in this case the hydroalcoholic extract of both plants was used.

Example 8

Metabolomic Analysis of Galeopsis segetum Neck and Galeopsis tetrahit L.

Aim of the Study:

In the present assay the phytochemical investigation of Galeopsis segetum Neck and Galeopsis tetrahit L. plant materials and extracts making use of the NMR fingerprinting technique is described.

The metabolomics comparison of the two species is described as well.

Materials and Methods:
Samples of Galeopsis sp. Under Exam

| ID number | Botanic ID | |
|---|---|---|
| 211973 | G. segetum (Ref. plant material) | Vegetal raw material |
| 211974 | G. segetum (Ref. plant material) | Vegetal raw material |
| 211975 | G. segetum (Ref. plant material) | Vegetal raw material |
| 211976 | G. segetum (Ref. plant material) | Vegetal raw material |
| 202517 | G. tetrahit (Ref. plant material) | Vegetal raw material |
| 202518 | G. tetrahit (Ref. plant material) | Vegetal raw material |
| 202519 | G. tetrahit (Ref. plant material) | Vegetal raw material |
| 203285 | G. tetrahit (Ref. plant material) | Vegetal raw material |

-continued

| ID number | Botanic ID | |
|---|---|---|
| 994/39/A | — | Extract |
| 1029/41/A | — | Extract |
| 1029/42/A | — | Extract |

Extraction Procedure for Vegetal Raw Material:

The milled raw material is extracted in 40% ethanol for 6 hours at 50° C. in a heated bath under mechanic stirring.

Each extract is then filtrated and the solvent is evaporated through lyophilisation.

Preparation of the Sample for the Analysis:

About 10 mg of each sample are weighed and dissolved in 1 mL of 40/60 MeOD 99.8%/buffered D2O (v/v, phosphate buffer, 100 µM).

The spectra are recorded on a NMR Varian 400 MHz and then undergo metabolomic analysis using Matlab software (Mathworks®).

The experimental parameters are reported below:

NMR Parameters:

| Parameter | Value |
|---|---|
| Acquisition Time (sec) | 3.9999 |
| Frequency (MHz) | 399.7839 |
| Nucleus | 1 H |
| Number of Transients | 32 |
| Original Points Count | 24752 |
| Points Count | 32768 |
| Pulse Sequence | wet1D |
| Receiver Gain | 42.00 |
| SW(cyclical) (Hz) | 6188.12 |
| Solvent | Buffered $D_2O$/Methanol 9.8% |
| Temperature (degree) | 30° C. |

Matlab Data Preprocessing:

Normalization to 100

Mean centering

Baseline correction to 0

Results and Conclusions

1H-NMR spectra have been registered and processed with VNMRJ 4.0 rev. Spectrus Platform from ACD/labs has been used for Fourier transformation and data set elaboration. Raw data obtained from NMR analyses were converted into a matrix represented by "n×m" data points, where "n" is the number of each spectrum and "m" is the value of each variable. Generally the number of variables consists of more than 15000 data points.

The data matrix was processed making use of a Principal Component Analysis (PCA) programmed on MATLAB software from The MathWorks (Natick, USA). The original spectra were previously aligned using COW (Correlation Optimized Warping) algorithm [Tomasi et al., J. Chemom. Vol. 8 (2004) 231-241]. COW algorithms are available online at http://www.models.life.ku.dk/algorithms. Signals underwent data centring, normalization to the percent of the total signal responses within each spectrum and baseline corrected. They were also alternatively subjected to autoscaling to the variance unit, in order to make each signal of the dataset directly comparable among all the spectra and to attribute the same importance to each peak of the spectrum: the resulting analysis was comparable with the unautoscaled results [Van den Berg et al. BMC Genomics vol. 7 (2006), 142].

Figure 6:
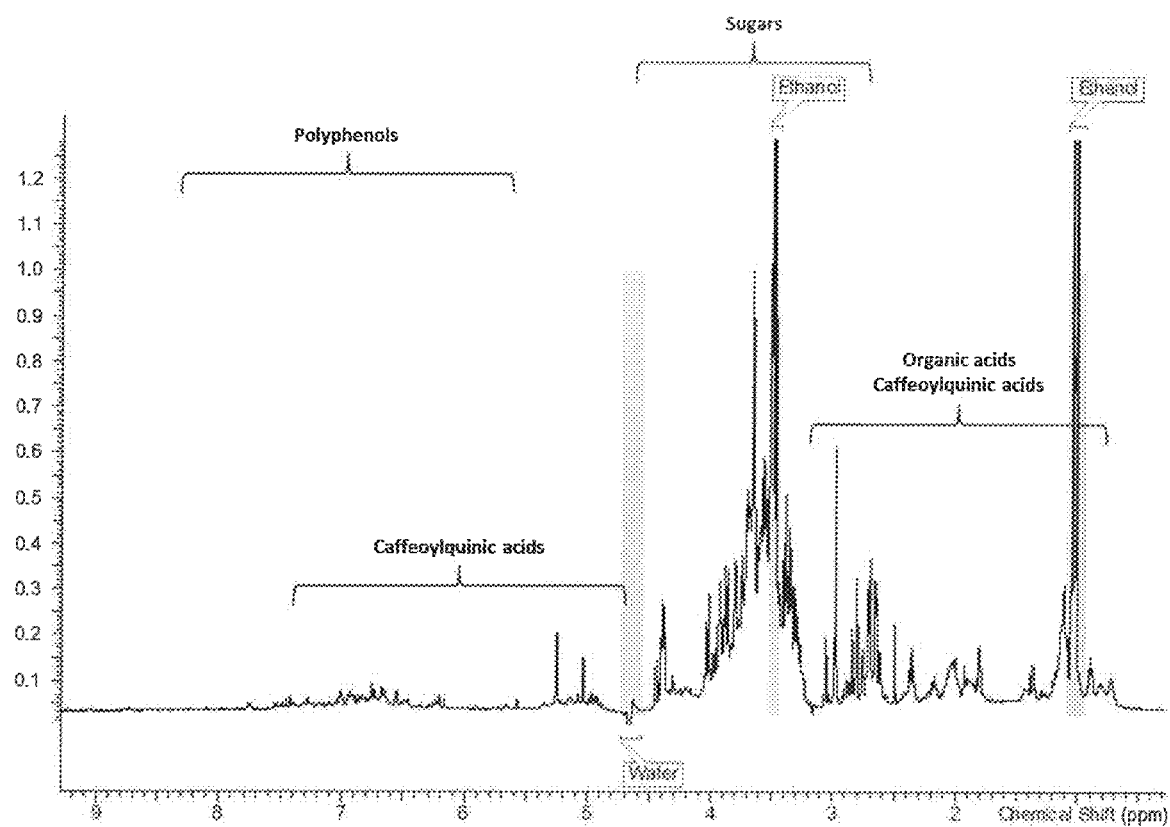
FIG. 6 shows the $^1$H-NMR spectrum of *Galeopsis* sp. aerial parts extract.

A typical 1H-NMR spectrum of *Galeopsis* sp. aerial parts extract is displayed in FIG. 6: The aligned and normalized 1H-NMR spectra relative to the samples under investigation were depleted of peaks belonging to the solvents and to sugars, which are useless for the comparison between raw material and extracts.

Figure 7:
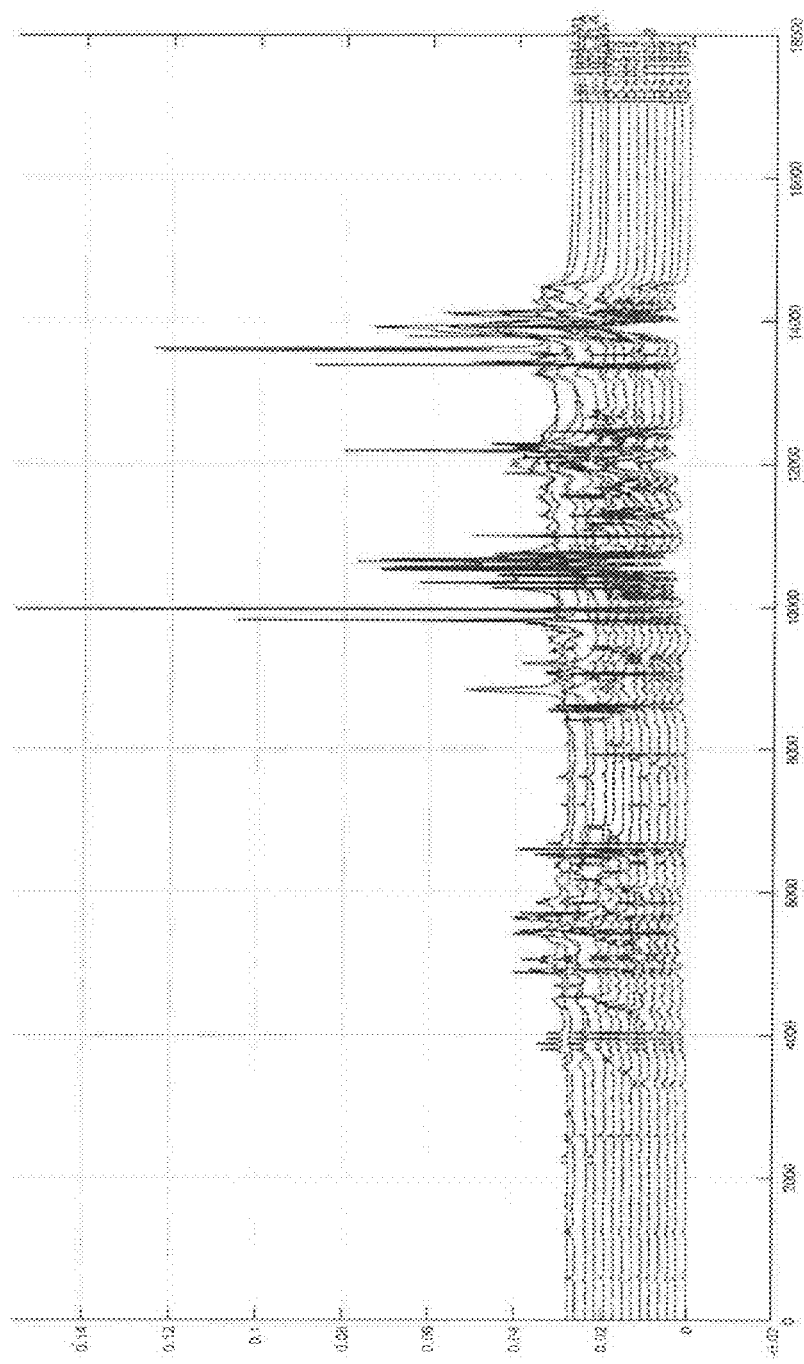
FIG. 7 shows the $^1$H-NMR spectra of the samples under the investigation made in Example 8.

The obtained spectra are reported in FIG. 7.

The 1H-NMR spectra were represented by a data matrix with 11 samples×16501 points of chemical shift intensities (variables) and submitted to multivariate evaluation making use of the Principal Component Analysis.

Figure 8:
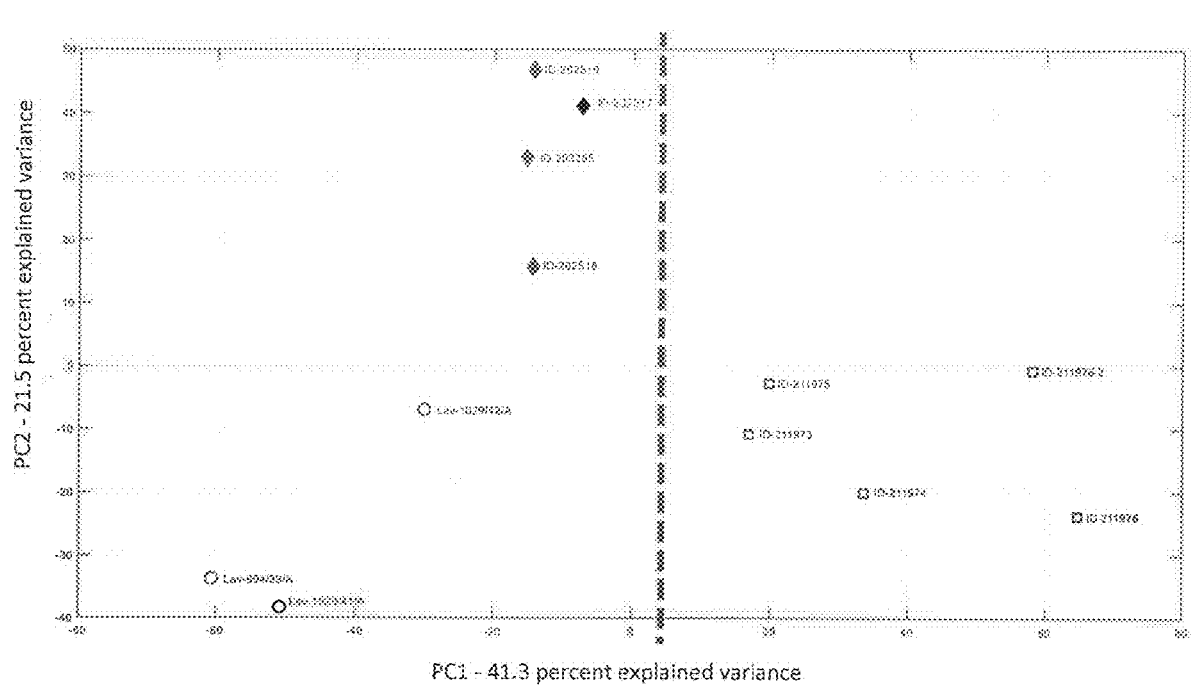
FIG. 8 shows the PC1 vs. PC2 projections of the $^1$H-NMR spectra of the plant materials of *Galeopsis segetum* and *Galeopsis tetrahit* and extracts of *Galeopsis tetrahit* as evidenced in Example 8.

The unsupervised PC1 vs PC2 projection of the 1H-NMR spectra belonging to *Galeopsis segetum* and *tetrahit* plant materials (green squares: *Galeopsis segetum* reference raw material, blue diamonds: *Galeopsis tetrahit* reference raw material) and *Galeopsis tetrahit* extracts (blank circles) are reported in FIG. 8.

Figure 9:
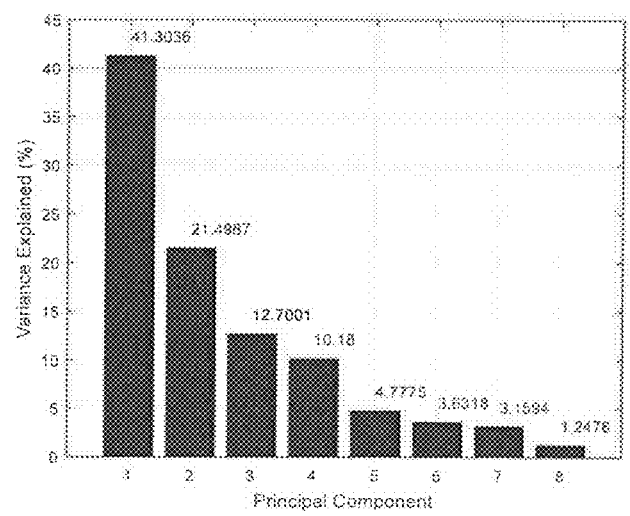
FIG. 9 shows the sum of PC1 and PC2 accounts for about 63% of the total variance.

The sum of PC1 and PC2 accounts for about 63% of the total variance (FIG. 9).

As reported in FIG. 8, the two clusters of *Galeopsis segetum* and *tetrahit* resulted to be separated along the PC1, which represents most of the variance of the dataset (41%). The extracts 1029/41/A, 1029/42/A and 994/39/A lay down in the space accounted for *G. tetrahit* reference raw material, suggesting the phytochemical composition similarity with the *Galeopsis tetrahit* species.

Figure 10:
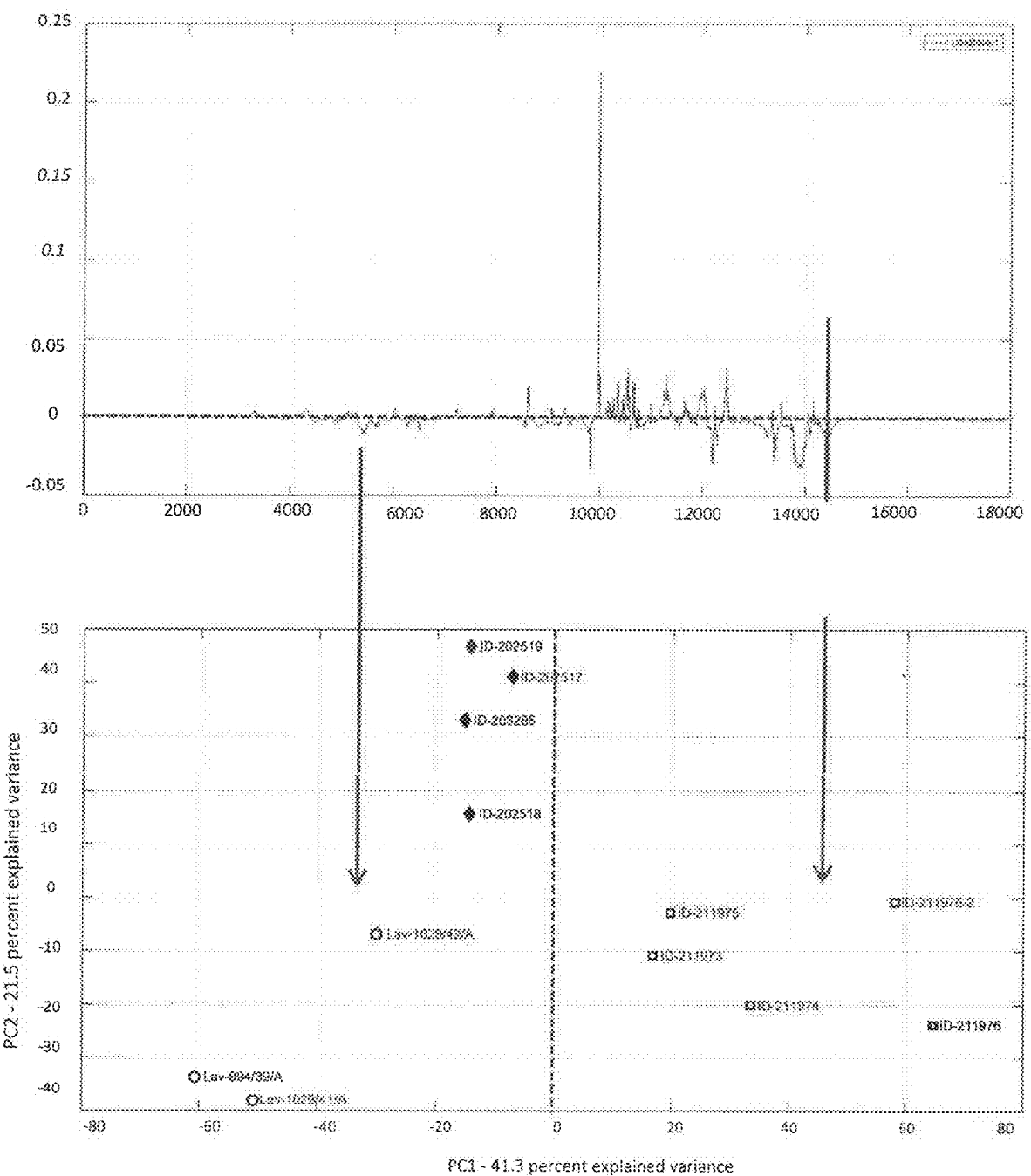
FIG. 10 shows the loadings plot of PC1 as described in Example 8.

In order to further investigate the obtained results, the loadings plot of PC1 has been evaluated. Loading 1 for PC1 helps assigning the variables (peaks) which are mostly responsible of the separation in the PC1 vs PC2 space. The loading 1 is reported in FIG. 10.

Loading 1 justifies the separation along the PC1: the right half of the PCA area (positive part) corresponds to the upper part of the loading 1 while the left zone of the PCA (negative part) corresponds to the bottom part of the loading.

Figure 11:
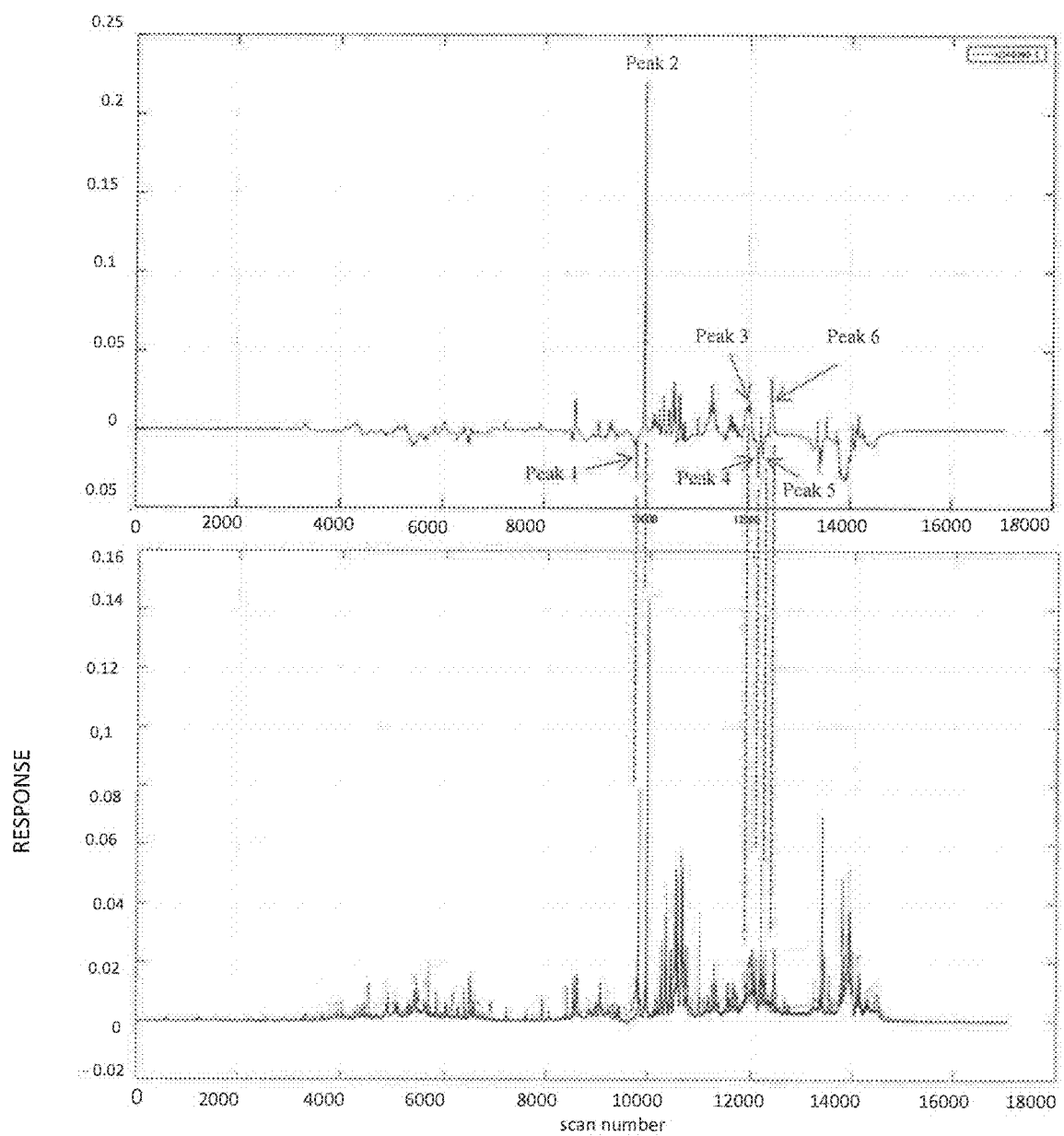
FIG. 11 illustrates the comparison of the NMR profile with loading 1 as reported in Example 8 to identify the NMR signals responsible of the PCA clustering separation.

Comparing the NMR profile with loading 1 is therefore possible to identify the NMR signals responsible of the PCA clustering separation, as reported in FIG. 11.

Peaks 1 and 2 can be tentatively assigned to the acetate moiety of the flavonoids group, typical of the *Segetum* species [Tomas-Barberan et al. BMC Genomics vol. 7 (2006), 142]. Peaks 3, 4, 5 and 6 are overlapping making difficult their attribution. Probably these signals belong to caffeic or caffeoylquinic acids.

Additionally, the NMR dataset was submitted to a supervised statistical analysis (PLS, Partial Least Squares), that allows to classify unknown samples using reference standard raw materials: this function allows to assign the unknown samples (in this case the extracts themselves) to one class out of the two reference clusters.

Figure 12:
FIG. 12 shows the data obtained from the statistical analysis PLS reported in Example 8.

The obtained data from this evaluation are shown in FIG. 12 (PLS plot) and in the following Table 1 (predicted values):

TABLE 1

| ID sample | Predicted value |
|---|---|
| 211973 | 1.0 |
| 211974 | 1.0 |
| 211975 | 1.2 |
| 211976 | 0.9 |
| 211976-2 | 1.1 |
| 202517 | 2.1 |
| 202518 | 1.9 |
| 202519 | 2.1 |
| 203285 | 1.9 |

TABLE 1-continued

| ID sample | Predicted value |
|---|---|
| 994/39/A | 1.8 |
| 1029/41/A | 1.6 |
| 1029/42/A | 1.7 |

Table 1 lists the predicted values for each sample of the dataset: since the clusters for *G. segetum* and *tetrahit* used as the training set were assigned with values respectively of 1 and 2, values close to 1 allow to assign the sample to the *segetum* class, while values close to 2 allow to assign the sample to the *tetrahit* cluster.

The obtained results outline that all the three extracts are ascribable to the *tetrahit* species. In conclusion, either the unsupervised and the supervised statistical methods used in this report support the following:

NMR analysis shows the differences in the phytochemical composition between *Galeopsis segetum* Neck. and *Galeopsis tetrahit* L. due to a different secondary metabolites pattern.

The extracts obtained from *Galeopsis tetrahit* plant material show equivalent secondary metabolites pattern as the starting plant material species, namely the *Galeopsis tetrahit*.

REFERENCES

Subirade I, Fernandez Y, Periquet A, Mitjavila S, 1995. Catechin protection of 3T3 Swiss fibroblasts in culture under oxidative stress. Biol Trace Elem Res 47(1-3), 313-319.

Kutuk O, Adli M, Poli G, Basaga H, 2004. Resveratrol protects against 4-HNE induced oxidative stress and apoptosis in Swiss 3T3 fibroblasts. Biofactors 20(1), 1-10.

Mosmann T, 1983. Rapid Colorimetric Assay for Cellular Growth and Survival: Application to Proliferation and Cytotoxicity Assays. J Immunol Methods 65(1-2), 55-63.

Rajapakse N, Mendis E, Byun H G, Kim S K, 2005. Purification and in vitro antioxidative effects of giant squid muscle peptides on free radical-mediated oxidative systems. J NutrBiochem 16(9), 562-569.

Coda R, Rizzello C G, Pinto D, Gobbetti M, 2012. Selected Lactic Acid Bacteria Synthesize Antioxidant Peptides during Sourdough Fermentation of Cereal Flours. Appl Environ Microbiol 78(4), 1087-1096.

Tobi S E, Paul N, McMillan T J, 2000. Glutathione modulates the level of free radicals produced in UVA-irradiated cells. J PhotochPhotobio B 57(2-3), 102-112

Chomczynski P, Mackey K. Modification of the TRI reagent procedure for isolation of RNA from polysaccharide- and proteoglycan-rich sources. Biotechniques 1995; 19:942-5.

The invention claimed is:

1. A method for treating hair loss or stimulating hair growth in a subject comprising orally administering or topically applying a composition comprising an amount of a plant extract of *Galeopsis tetrahit* species effective for treating hair loss or stimulating hair growth and a physiologically acceptable carrier.

2. The method according to claim 1 wherein said composition is in a form for oral administration or topical application.

3. The method according to claim 1 wherein said composition is in a form for topical administration selected from the group consisting of a solution, a lotion, an emulsion, a shampoo, a cream and an ointment.

4. The method according to claim 1 wherein said composition is in a form for oral administration selected from the group consisting of a tablet, a capsule, a pill and a granulated powder.

5. The method according to claim 1 wherein the composition further comprises at least one active biological ingredient selected from the group consisting of a vitamin, a mineral, a micronutrient and a mixture thereof.

6. The method according to claim 4, wherein the composition is a nutraceutical product, a functional food, a dietary integrator or a food supplement.

7. The method according to claim 1 wherein said composition further comprises an effective amount of an extract from *Galeopsis segetum* Necker.

8. The method according to claim 1 wherein the plant extract is obtained by extraction with a physiologically acceptable solvent from a portion or tissue of *Galeopsis tetrahit*.

9. The method according to claim 1 wherein the hair loss is provoked by rogenetic alopecia or defluvium telogenicum.

10. The method of claim 1 further comprising hair filling acid increasing volume of hair of said subject.

* * * * *